United States Patent [19]
Tixier

[11] 3,956,272
[45] May 11, 1976

[54] POLYSACCHARIDE GELS

[76] Inventor: Rene Tixier, 24 rue des Cordelieres, Paris 13e, France

[22] Filed: Apr. 30, 1973

[21] Appl. No.: 355,481

[30] Foreign Application Priority Data
May 1, 1972 United Kingdom............. 20091/72

[52] U.S. Cl. .................... 260/209 R; 260/211.5 R; 424/2; 424/12
[51] Int. Cl.² ........................................ C08B 37/00
[58] Field of Search ................ 260/209 R, 211.5 R

[56] References Cited
UNITED STATES PATENTS

| | | |
|---|---|---|
| 3,021,329 | 2/1962 | Borchert ........................ 260/209 R |
| 3,455,895 | 7/1969 | Niilo-Rama et al. ............ 260/209 R |
| 3,507,851 | 4/1970 | Ghetie et al. ................... 260/209 R |
| 3,637,685 | 1/1972 | D'Alelio .......................... 260/210 R |
| 3,651,043 | 3/1972 | Schell et al. .................... 260/209 R |

*Primary Examiner*—Johnnie R. Brown
*Attorney, Agent, or Firm*—Haseltine, Lake & Waters

[57] ABSTRACT

A process for the treatment of polysaccharide gels, especially of agarose or gelose, comprises bridging the linear polysaccharide chains with 2,4,6-trichloro-1,3,5-triazine, e.g. by suspending the polysaccharide gel in a solution of 2,4,6-trichloro-1,3,5-triazine and reacting the two ingredients. The polysaccharide gel may be in the form of pearls, plates or granules. The gels are useful in immuno-electrophoresis processes.

4 Claims, 1 Drawing Figure

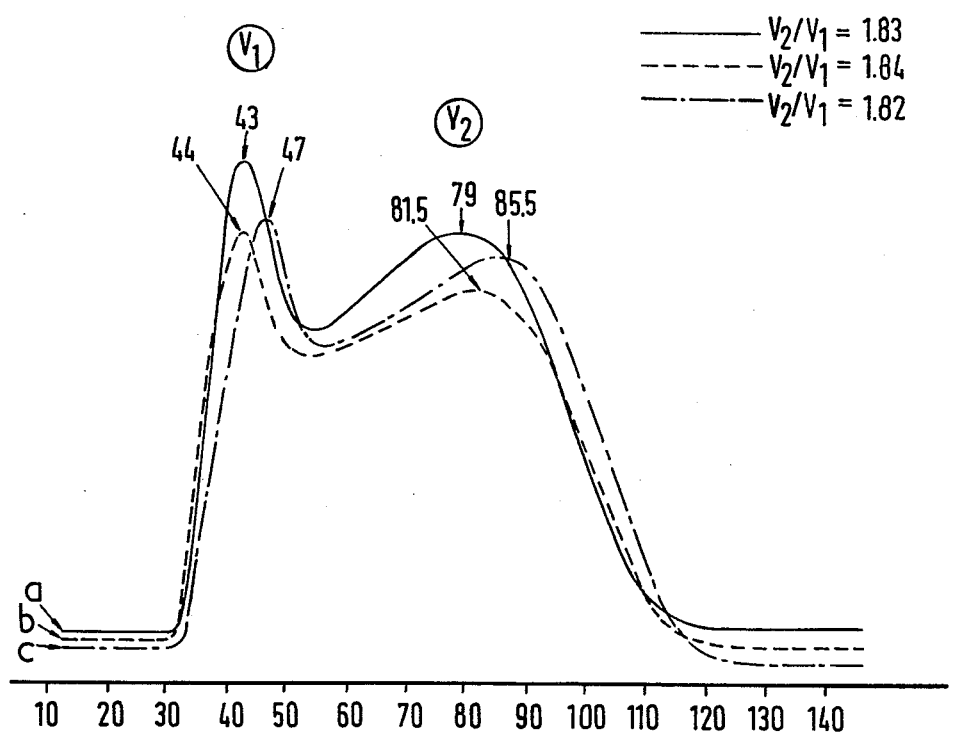

POLYSACCHARIDE GELS

This invention is concerned with improvements in and relating to polysaccharide gels having improved physicochemical properties and a process for the production of such gels.

Gelose (or agar-agar) and agarose (a neutral polysaccharide isolated from gelose) are currently used either in the forms of plates of the hydrated gel in immuno-diffusion, electrophoresis or immuno-electrophoresis processes, or in the form of granules for the separation of nautral substances by molecular exclusion chromatography. Further, they are also used, in the granular form, as supports for the chemical binding of enzymes (to give insoluble enzymes), various substances (selective chromatography) or substances having ionizable groups (ion-exchange chromatography).

These gels, in their different forms, must be used at temperatures below 50°C in the hydrated state and these factors limit their range of use and their commercial application.

The formation of a gel in water is due principally to the presence of hydrogen bonds which bind the polysaccharride chains into the form of a three dimensional net. These bonds are very fragile and, consequently, readily dissociated by physical or chemical agents. Thus, gelose or agarose do not form gels at extreme pH values (either acidic or basic), at a temperature above about 50°C, or in the presence of certain chemical substances such as urea. This natural fragility of the gels limits their use both in electrophoresis and chromatograph, as well as for use as a support for enzymes.

In chromatography, the granules or pearls cannot be sterilized by heat and this is a major inconvenience when one is concerned with the separation of viruses or other biological substances which should be handled under aseptic conditions. Further, when the granules are used as supports for enzymes, it is not possible to use them when the temperature of the reaction medium rises above 40°C.

In electrophoresis, the solutions of gelose or agarose used are of a low concentration (generally lower than 2%) so that the gels obtained on cooling are soft and consequently very fragile. It is, therefore, necessary to flow the solutions onto glass plates and to take considerable precautions in handling the gels and in storing the electrophoretograms. These latter, after drying, give particularly fragile films.

It has now been found, in accordance with the present invention, that it is possible to treat polysaccharide gels, such as agarose or gelose gels, so that they do not lose their principal physico-chemical properties but do acquire a resistance to agents which weaken the hydrogen bonds. Basically, the process of the invention comprises reacting the polysaccharide gel with 2,4,6-trichloro-1,3,5-triazine so that the lateral labile hydrogen bonds are replaced by stable chemical bonds bridging the linear polysaccharide chains.

The process of the invention is conveniently carried out by suspendng the polysaccharide gel in a solution of 2,4,6-trichloro-1,3,5-triazine and reacting the two ingredients, preferably at an elevated temperature of the order of about 5°C. The reaction medium conveniently consists of water or a mixture of water and a water-miscible organic solvent such as acetone or dioxane.

The treated gels, obtained in accordance with the invention, have essentially the same characteristics as untreated gels of the same concentration, in particular, the power of resolution with respect to compounds under test remains unchanged. For example, the molecular selectivity curves obtained with gels treated in accordance with the invention and containing 2, 4 or 6% of agarose are essentially superimposable on those given by conventional gels containing the same amounts of agarose. Sterilization of the treated gels at 120°C for 15 minutes in an autoclave gives rise to no change in the chromatographic properties of the treated gels. Further, plates of gels treated according to the invention maintain their physico-chemical properties and may be used in electroporesis, immuno-diffusion or immuno-electrophoresis processes, whilst at the same time they possess certain new physical properties in that they are more flexible under resistance and hence can be readily manipulated without the aid of a ridge or support. Such plates also can be sterilized at a 120°C in an autoclave.

In order that the invention may be well understood, the following Examples are given by way of illustration only.

EXAMPLE 1

200 ml of a 2% gel of agarose or gelose is suspended in a solution of 5 grams trichlorotriazine in a mixture of 75 ml of acetone and 25 ml of water, previously heated to 50°C. The mixture is stirred for 90 minutes and then the hydrochloric acid formed during the reaction is neutralized with aqueous sodium hydroxide solution. The gel is then washed with demineralized water to remove acetone and secondary reaction products as well as excess trichlorotriazine.

The gel is resuspended in 100 ml of normal sodium hydroxide solution. After the addition of 0.500 grams of sodium borohydrate the suspension is maintained at a temperature of about 90°C for 1 hour. The thus-treated gel is then washed with warm water and resuspended in cold water and the pH of the suspension adjusted to 4 by the addition of acetic acid. The acidified suspension is stirred for 15 minutes then again washed with demineralized water and finally dried under vacuum.

The above procedure may be repeated using gels of strengths other than 2% and thus, for example, in the case of a 4% gel the procedure may be repeated using 8 grams of trichlorotriazine per 200 ml of gel, and for a 6% gel using 12 grams of trichlorotriazine per 200 ml of gel.

The gels prepared by the above process have the same properties as conventional gels having the same concentration of agarose or gelose.

This is shown by comparative exclusion chromatography tests carried out with a 4% agarose gel in the form of beads having a diameter of from 100 to 160 microns, the beads under test being those before and after treatment with trichlorotriazine and after sterilization at 120°C for 30 minutes. A 0.5 molar solution of blue dextran-2000 in tris-(hydroxymethyl)-aminomethamne-HCl, having a pH of 7.4, whilst passed over columns of the gels having a diameter of 20 ml and a height of 400 ml. The elution curves obtained were substantially identical for the three forms of gel, thus illustrating that the resolving power of the 4% agarose gel was not substantially modified by treatment with trichlorotriazine or by a following sterilisation of the treated gel. These curves are shown in FIG. 1 of the accompanying drawings.

EXAMPLE 2

200 ml of a 2% gel of gelose or agarose are suspended in 100 ml of demineralized water. 6 grams of trichlorotriazine are dissolved in 100 ml of dioxane and this solution is slowly poured into the suspension, with agitation, at ambient temperature. After stirring for about 10 minutes the suspension is neutralized with the aid of normal sodium hydroxide solution, the agitation and neutralization are continued until the pH stabilizes at 7.

The neutralized suspension is then heated for 1 hour at 60°–65°C whilst neutralizing the acid formed by the reaction between the trichlorotriazine and the agarose. The suspension is then cooled and the gel washed until free of chloride ion. The washed gel is then resuspended in 100 ml of normal sodium hydroxide solution and treated with sodium borohydrate in the manner described in Example 1.

The above procedure may be carried out for gels of greater strength using 8 grams of trichlorotriazine for 200 ml of a 4% gel and 12 grams of trichlorotriazine for 200 ml of a 6% gel.

Elution curves obtained with blue-dextran 2000 show that pearls of 4% agarose gel, after treatment and sterilization as described above, have the same resolution power as non-treated pearls.

EXAMPLE 3

200 ml of a 2% agarose or gelose gel are suspended in 1000 ml of demineralized water. 6 grams of trichlorotriazine are dissolved in 150 ml of acetone and the resulting solution added to the gel suspension. The reaction mixture is then slowly heated to a temperature of about 60°C at which temperature there are added thereto 90 ml of normal sodium hydroxide solution and 1 gram of sodium borohydrate. The mixture is stirred at 60°C for 1 hour. After cooling, the gel is washed with water until free of chloride ion and then dried in a vacuum. The above procedure may be repeated on stronger gels using, for example, 8 grams of trichlorotriazine per 200 ml of 4% gel and 12 grams of trichlorotriazine per 200 ml of 6% gel.

EXAMPLE 4

150 mg of trichlorotriazine are dissolved in 2.5 ml of acetone. A 1.5% solution of agarose (or gelose) in 100 ml of 0.1 molar trisodium citrate is prepared. The trichlorotriazine solution is added to the agarose (or gelose) solution which has previously been heated to 50°C. The temperatures of the reaction mixture is then raised, with stirring, to 70°C at which temperature 25 ml of normal sodium hydroxide solution (previously heated to 70°C) are added thereto. The mixture is flowed or poured into plastic boxes to obtain layers of gel 2 mm thick (4 boxes of 8.2 × 13.5 mm for 100 ml of gel). Polymerization is complete after about 15 hours at ambient temperature. The plates are then washed with warm water (about 70°C) until neutral.

I claim:

1. A strengthened polysaccharide gel obtained by reacting a polysaccharide gel selected from the group consisting of gelose and agarose, with 2,4,6-trichloro-1,3,5-triazine.
2. The gel of claim 1 in the form of pearls.
3. The gel of claim 1 in the form of plates.
4. The gel of claim 1 in the form of granules.

* * * * *